US008921577B2

(12) United States Patent
Balaram et al.

(10) Patent No.: US 8,921,577 B2
(45) Date of Patent: Dec. 30, 2014

(54) CHOLECYSTOKININ RECEPTOR LIGANDS

(75) Inventors: Padijarethakkal N Balaram, Cochin (IN); Pornthip Lattmann, Birmingham (GB)

(73) Assignee: PNB Vesper Life Sciences Pvt. Ltd., Cochin (IN)

( * ) Notice: Subject to any disclaimer, the term of this patent is extended or adjusted under 35 U.S.C. 154(b) by 0 days.

(21) Appl. No.: 13/989,790

(22) PCT Filed: Jul. 2, 2012

(86) PCT No.: PCT/IN2012/000469
§ 371 (c)(1),
(2), (4) Date: May 25, 2013

(87) PCT Pub. No.: WO2014/006629
PCT Pub. Date: Jan. 9, 2014

(65) Prior Publication Data
US 2014/0005248 A1    Jan. 2, 2014

(51) Int. Cl.
*C07D 207/38*    (2006.01)
*C07D 207/273*    (2006.01)

(52) U.S. Cl.
CPC .......... *C07D 207/38* (2013.01); *C07D 207/273* (2013.01)
USPC ......................................... 548/544; 514/425

(58) Field of Classification Search
CPC .......................... C07D 207/273; C07D 207/38
USPC .......................................... 548/544; 514/425
See application file for complete search history.

(56) References Cited

U.S. PATENT DOCUMENTS 6,444,665 B1    9/2002    Helton et al.

OTHER PUBLICATIONS

International Search Report and Written Opinion for PCT/IN2012/000469 dated Jan. 25, 2013.
Chihab-Eddine et al., Synthesis and reactivity of (IS)-N-(1-phenylethyl) maleimide towards nucleophiles, Tetrahedron Letters, 2001,42:573-576.
Lattmann et al.,Cholecystokinin antagonists (part 1): Antinociceptive, anxiolytic and antidepressant effects, Drug Discov Ther,2008; 2(3):156-167.
Lattmann et al., Part 2. Long term in vivo/in vitro evaluation of the Cholecystokinin antagonists:Drug Discov Ther, 2008; 2(6):344-352.
Lattmann et al., Synthesis and evaluation of N-(3-oxo-2,3-dihydro-1Hpyrazol-4-yl)-1H-indole-carboxamides, Journal of Pharmacy and Pharmacology, 2006, 58: 393-401.
Offel et al., Synthesis of Substituted 3-Anilino-5-phenyl-1,3-dihydro-2H-1,4-benzodiazepine-2-ones, Arch. Pharm. Chem. Life Sci. 2006, 339, 163-173.
Singh et al., Antidepressant/Anxiolytic and Anti-Nociceptive effects of novel 2-substituted 1,4-benzodiazepines-2-ones, Sci Pharm. 2010; 78: 155-169.

*Primary Examiner* — Robert Havlin

(57) ABSTRACT

The present invention relates to novel 5-hydroxy-5-aryl-pyrrol-2-ones, their preparation and their use as non-peptide CCK ligands, particularly in pharmaceutical formulations thereof.

16 Claims, No Drawings

CHOLECYSTOKININ RECEPTOR LIGANDS

CLAIM OF PRIORITY

This application is a U.S. national stage filing under 35 U.S.C. §371 of International Application No. PCT/IN2012/000469 filed on Jul. 2, 2012 entitled "Novel Cholecystokinin Receptor Ligands", which is incorporated herein by reference in its entirety.

FIELD OF THE INVENTION

The present invention relates to novel 5-hydroxy-5-aryl-pyrrol-2-ones, their preparation and their use as non-peptide CCK ligands, particularly in pharmaceutical formulations thereof.

BACKGROUND OF THE INVENTION

Cholecystokinins (CCKs) act as anti-opioid peptides. CCK was initially described as a regulatory hormone found in endocrine cells of the gastro-intestinal (GI) tract. Some CCKs share a common amino acid sequence with gastrin, which is involved in control of gastric acid and pepsin secretion. CCKs have also been found throughout the central nervous system (CNS), where they act as neurotransmitter and/or modulator of many important functions. There are various known structures of CCK, identified with reference to the number of amino acids they comprise. For example, CCK-8 a naturally-occurring predominant CCK peptide having only eight amino acids, is the minimum fully-active sequence. Albeit, small amounts of CCK-4 have also been reported.

CCKs have multiple function in the physiology and pathology of vertebrate. Pharmaceuticals and biotechs have taken advantage of the pathological properties of the CCKs to develop molecules that block these properties to deliver health and wellness. For instance, CCK plays an important role in the invasiveness and the production of matrix metalloproteinase-9 (MMP-9) in human pancreatic cancer cell lines. The pathway of the invasiveness may be associated with MMP-9 of those lines regulated by CCK.

The gut hormone CCK exerts various actions on the gastrointestinal tract, including the regulation of growth. The hormone has been reported to induce hypertrophy and hyperplasia of the pancreas and to enhance chemically-induced pancreatic carcinogenesis in animals. Stimulation of endogenous CCK secretion through the induction of deficiency of intraintestinal proteases and bile salts by trypsin-inhibiting nutrients, bile salt-binding drugs or surgical intervention is also capable of stimulating growth and tumour development in the rat. In humans, factors suggested to increase the risk of pancreatic cancer, such as a high-fat- and high-protein-diet or gastrectomy, are known to stimulate plasma CCK secretion. Receptors for CCK have been demonstrated in human pancreatic adenocarcinomas, and CCK has been demonstrated to enhance the pancreatic xenograft growth and growth of gastric and bile duct cancer.

The actions of CCK are mediated by two G protein coupled receptor (GPCRs). They are termed as type-A and type-B, reflecting their preferential localisation in the alimentary tract and in the brain, respectively. Recently, these receptors have been re-named as CCK1 and CCK2, respectively, although the original designation is also used hereinbelow with respect to the present invention. The molecular cloning of two CCK receptor subtypes, one from rat and human pancreas and one from human brain, has confirmed the pharmacological classification of the CCK receptors. The differential distribution of CCK1 and CCK2 receptors in the peripheral vs. central nervous system is not absolute, as CCK1 receptors have also been shown to be expressed in discrete regions of the CNS, including the spinal cord, particularly in primates.

The functions of the CCK1 receptor in the brain are poorly understood, whereas the CCK2 receptor is known to mediate anxiety, panic attacks, satiety and pain. Therefore, antagonists to CCK receptors and to gastrin have been useful to prevent and treat CCK-related and/or gastrin-related disorders. Just as there are some overlap in the biological activities of CCK and gastrin, antagonists also tend to have affinity for both receptors.

Selective CCK receptor antagonists are themselves useful in treating CCK-related disorders of the appetite regulatory systems as well as in potentiating and prolonging opiate-mediated analgesia, thus having utility in the treatment of pain, while selective gastrin antagonists are useful in the modulation of CNS behaviour, as a palliative for gastrointestinal neoplasms, and in the treatment and prevention of gastrin-related disorders of the GI system in humans and animals, such as peptic ulcers, Zollinger-Ellison syndrome, antral G cell hyperplasia and other conditions in which reduced gastrin activity is of therapeutic value. Also, since CCK and gastrin also have trophic effects on certain tumours, antagonists of CCK and gastrin are useful in treating these tumours.

Various chemical classes of CCK-receptor antagonists have been reported. These include pyrazolidinones showing good selectivity for $CCK_B$ receptors (Howbert, J. J. et. al.; *Bioorg. Med. Chem. Lett.* 1993, 3, 875-880.), ureidoacetamides which are potent and selective ligands for $CCK_B$/gastrin receptors (WO 91/113874), ureidophenoxyacetanilides (Takeda, Y. et. al.; *Chem. Pharm Bull.* 1998, 46, 951-961), ureidomethylcarbamoylphenylketones (Hagishita, S.; et. al., *Bioorg. Med. Chem.* 1997, 5, 1695-1714), and ureidobenzodiazepine derivatives (Evans, B. E.; et. al., *Proc. Natl. Acad. Sci. USA* 1986, 83, 4918-4922).

SUMMARY OF THE PRESENT INVENTION

The objective of the present invention is to provide novel 5-hydroxy-5-aryl-pyrrol-2-ones derivatives, which preferably act as CCK ligands, and pharmaceutical formulations thereof.

According to the present invention there is provided a compound of formula (I):

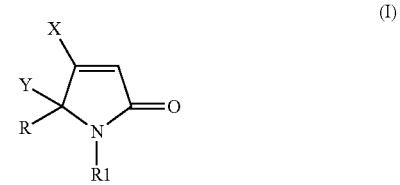

wherein

X is selected from hydrogen, a hydroxyl group, a halogen, a substituted or unsubstituted cyclic and heterocyclic moiety, substituted or unsubstituted, linear or branched alkyl, alkyloxy, alkylcarbonyl, alkyloxycarbonyl, alkenyl, alkenyloxy, alkenylcarbonyl, alkenyloxycarbonyl, alkynyl, alkynyloxy, alkynylcarbonyl, alkynyloxycarbonyl, aryl, benzyl, arlyoxy, arylcarbonyl, aryloxycarbonyl and sulphur equivalents of said oxy, carbonyl and oxycarbonyl moieties or as defined for Y, R and R1.

Y is selected from H, hydroxyl, thio, substituted N as defined in R, R1 and X.

R is selected from hydrogen, a halogen, an amide, a substituted or unsubstituted cyclic and heterocyclic moiety, a phenyl group, aryl, substituted or unsubstituted, linear or branched alkyl, alkyloxy, alkylcarbonyl, alkyloxycarbonyl, alkenyl, alkenyloxy, alkenylcarbonyl, alkenyloxycarbonyl, alkynyl, alkynyloxy, alkynylcarbonyl, alkynyloxycarbonyl, aryl, benzyl, arlyoxy, arylcarbonyl, aryloxycarbonyl and sulphur equivalents of said oxy, carbonyl and oxycarbonyl moieties, and as in R1, Y and X defined.

$R^1$ is selected from H, methyl, alkyl, aryl, substituted aryl, benzyl, $C_{1-18}$ straight, branched or cyclic, saturated, unsaturated and aromatic hydrocarbyl groups, which aromatic groups may be heterocyclic, cyclic or acyclic and which may optionally be substituted by alkyl, alkoxy, or halo; or $R^1$ and $R^2$, when taken together with the N-atom to which they are bonded, may form an N-containing saturated, unsaturated or partially unsaturated ring system comprising 3 to 10 ring atoms selected from C, N and O, optionally substituted at any position of the ring by a substituent selected from a halogen, a substituted or unsubstituted cyclic and heterocyclic moiety, substituted or unsubstituted, linear or branched alkyl, alkyloxy, alkylcarbonyl, alkyloxycarbonyl, alkenyl, alkenyloxy, alkenylcarbonyl, alkenyloxycarbonyl, alkynyl, alkynyloxy, alkynylcarbonyl, alkynyloxycarbonyl, aryl, benzyl, arlyoxy, arylcarbonyl, aryloxycarbonyl, sulphur equivalents of said oxy, carbonyl and oxycarbonyl moieties, and as defined for the other substituents and any possible combination thereof.

Preferably said alkyl- and aryl containing moieties, more preferably $C_1$-$C_{12}$ connected to an aromatic system and most preferably is phenyl ethyl or substituted phenyl ethyl groups.

Preferred substituents for R are phenyl, substituted phenyl formed by $R^1$ alkyl or alkoxy, phenyl, benzyl, phenyl ($C_{2-4}$) alkenyl, phenoxy, benzyloxy, halo, oxo or alkyloxycarbonyl.

Suitable substituents on the aromatic system are methyl, halogen, benzyl, phenyl, alkoxycarbonyl and oxo. Preferably, said heterocyclic ring is mono- or di-substituted.

Preferably, X is H, halo (F, Br, Cl, I) or methyl.

Preferably, R is H, phenyl, halo, substituted phenyl, aryl and bis aryl, substituted aryl and heteroaryl.

It will be understood that formula (I) is intended to embrace all possible isomers, including optical isomers and mixtures thereof, including racemates. It will also be understood that formula (I) is intended to embrace all possible polymorphs, crystal, impurity, N-oxide, ester, hydrate or any combination thereof. In addition, the present invention includes within its scope prodrugs of the compounds of formula (I). In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed H. Bungaard, Elsevier, 1985.

The scope of the invention also extends to salts, particularly physiologically acceptable salts and hydrates of the compounds of formula (I).

The pharmaceutically acceptable salts of the compounds of formula (I) include the conventional non-toxic salts or the quarternary ammonium salts of the compounds of formula (I) formed, eg, from non-toxic inorganic or organic acids. The pharmaceutically acceptable salts of formula (I) also include those formed from a base, such as an alkali or alkaline earth metal hydroxide, or an organic base, such as an amine or a quarternary ammonium hydroxide. Some of the synthesized chemical structures that demonstrated significant CCK antagonistic properties are given below.

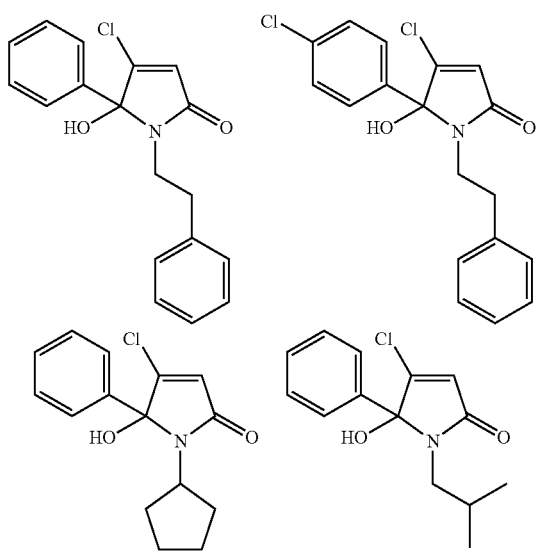

The present invention also resides in the use of a compound of the first aspect as a CCK receptor ligand and/or as a CCK antagonist. Preferably, said use is as a selective or mixed CCK1 or CCK2 ligand. Most preferred are mixed antagonists as reported in Lattmann et al.

[Lattmann, E., Arayarat, P. and Singh, H. (2000)
Review article: Small organic molecules as cholecystokinin antagonists.
*Science* (KKU), 28, 288-299

Lattmann, E., Billington, D. C., Poyner, D. R., Howitt, S. B. and Offel M. (2001)
Synthesis and evaluation of Asperlicin analogues as non-peptidal Cholecystokinin-antagonists. *Drug Design and Discovery*, 17, 219-230

Lattmann, E., Billington, D. C., Poyner, D. R., Howitt, S. B. and Offel, M. (2001)
Solid phase synthesis of 3-alkylated 1,4-benzodiazepines as non-peptidal Cholecystokinin antagonists. *Pharm. Pharm. Lett.* 11, 5-8

Lattmann, E., Billington, D. C., Poyner, D. R., Arayarat, P., Howitt, S. B., Lawrence, S. and Offel, M. (2002)
Combinatorial solid phase synthesis of multiply-substituted 1,4-benzodiazepines and affinity studies on the CCK2 receptor (Part 1). *Drug Design and Discovery*, 18, 9-21.

Lattmann, E., Sattayasai, J., Billington, D. C., Poyner, D. R., Puapairoj, P., Tiamkao, S., Airarat, W., Singh, H. and Offel, M. (2002)
Synthesis and evaluation of $N_1$-substituted-3-propyl-1,4-benzodiazepine-2-ones as Cholecystokinin ($CCK_2$)-receptor ligands. *J. Pharm. Pharm.* 54, 827-834

Lattmann, E., Arayarat, P. (2003)
Review article: From CNS-drugs to anti-neoplastic agents: Cholecystokinin (CCK)-antagonists as modern anti-cancer agents. Science (KKU) 2003, 31, 178-193

Lattmann, E., Sattayasai, J., Boonprakob, J., Lattmann, P., Singh, H. (2005)
Synthesis and evaluation of N-(5-methyl-3-oxo1,2-diphenyl-2,3-dihydro-1H-pyrazol-4yl)-N-phenylureas as Cholecystokinin antagonists *Drug Res./Arzneimittelforschung* 55, 251-258

Eric Lattmann, Harjit Singh, Yodchai Boonprakob, Pornthip Lattmann, Jintana Sattayasai (2006) Synthesis and evaluation of N-(3oxo-2,3-dihydro-1Hpyrazol-4-yl)-1H-indole-carboxamide as cholecystokinin antagonists,

*J. Pharm. Pharm.* 2006, 58, 1-9

Michael Offel, Pornthip Lattmann, Harjit Singh, David C. Billington, Yodchai Bunprakob, Jintana Sattayasai, Eric Lattmann (2006) Synthesis of substituted 3-anilino-5-phenyl-1,3-dihydro-2H-1,4-benzodiazepinones and their evaluation as cholecystokinin ligands

*Archiv der Pharmazie—Chemistry in Life Science,* 339, 163-173

Eric Lattmann, Jintana Sattayasai, Pornthip Lattmann, David C. Billington, Carl H. Schwalbe, Jordchai Boonprakob, Wanchai Airarat, Harjit Singh, and Michael Offel (2007) Anti-depressant and anti-nociceptive effects of 1,4-Benzodiazepine-2-ones based Cholecystokinin ($CCK_2$) antagonists, *Drug Discov Ther* 1(1): 45-56

Eric Lattmann, Jintana Sattayasai, Yodchai Boonprakob, Harjit Singh, Pornthip Lattmann and Simon Dunn (2008) Cholecystokinin antagonists (part 1): Antinociceptive, anxiolytic and antidepressant effects of N-(5-methyl-3-oxo-1,2-diphenyl-2,3-dihydro-1H-pyrazol-4-yl)-N'-phenylureas and carboxamides (2008) *Drug Discov Ther.* 2, (3) 156-167.

Eric Lattmann, Yodchai Boonprakob and Jintana Sattayasai (2008)

Part 2. Long term in vivo/in vitro evaluation of the Cholecystokinin antagonists: N-(5-methyl-3-oxo-1,2-diphenyl-2,3-dihydro-1H-pyrazol-4-yl)-N'-phenylurea MPP and carboxamide MPM (2008) *Drug Discov Ther.* 2, (6) 344-352.]

The ability of the compounds of formula (I) to antagonise CCK by acting as CCK-receptor ligands makes these compounds useful as pharmacological agents for the treatment and prevention of disorders wherein CCK and/or gastrin may be involved.

Therefore the present invention in a second aspect resides in a method of prevention or treatment of a mammal afflicted with a CCK-related condition, or prophylaxis in a mammal at risk of a CCK-related condition by administration of a therapeutically effective amount of a compound of the first aspect of the invention.

The invention also resides in a pharmaceutical formulation comprising a compound of said first aspect in admixture with a pharmaceutically acceptable carrier therefor.

The invention further resides in the use of a compound of the first aspect in the preparation of a medicament, particularly a medicament for the prevention or treatment or prophylaxis of a CCK-related disorder.

Examples of CCK-related conditions include GI disorders, especially such as irritable bowel syndrome, crohn's disease, gastro-oesophageal reflux disease or ulcers, excess pancreatic or gastric secretion, acute pancreitis, or motility disorders; CNS disorders caused by CCK interactions with dopamine, such as neuroleptic disorders, tardive dyskinesia, Parkinson's disease, psychosis or Gilles de la Tourette syndrome; disorders of appetite regulatory systems; Zollinger-Ellison syndrome; antral G cell hyperplasia; or pain (potentiation of opiate analgesia) including neuropathic pain The prevention and treatment of opiate-resistant severe clinical pain may represent an important aspect of the CNS applications, but other applications based on the interaction between CCK and dopamine in forebrain could also deserve clinical exploration.

The compounds of the invention may further be useful in the treatment or prevention of additional central nervous system disorders including neurological and psychiatric disorders. Example of such central nervous system disorders include anxiety disorders and panic disorders, wherein CCK is involved. Additional examples of central nervous system disorders include panic syndrome, anticipatory anxiety, phobic anxiety, panic anxiety, chronic anxiety and endogeneous anxiety.

Extensive research with respect to the use as antidepressants, anxiolytics, analgesics is published in the literature by E. Lattmann et al.

The compounds of the invention may further be useful in the prevention and treatment of oncologic disorders. Examples of such oncologic disorders include small cell adenocarcinomas and primary tumours of the central nervous system glial and neuronal cells. Example of such adenocarcinomas and tumours include, but are not limited to, tumours of the lower oesophagus, stomach, intestine, colon and lung, including small cell lung carcinoma, pancreatic carcinoma and others.

The compounds of the invention may further be used to control pupil constriction in the eye. The compounds may be used for therapeutic purposes during eye examinations and intra-ocular surgery in order to prevent miosis. They may further be used to inhibit miosis occurring in association with iritis, uveitis and trauma.

The compounds of the invention may further be used to prevent or treat eating disorders, body weight, fat and muscle mass related problems such as obesity, anorexia, cachexia, sarcopenia and others.

The compounds of the invention may further be useful for preventing or treating the withdrawal response produced by chronic treatment or abuse of drugs or alcohol. Such drugs include, but are not limited to, cocaine, alcohol or nicotine.

CCK antagonists potentiate the analgesic activity of opiates (Lattmann et al).

The compounds of the invention may also be useful as neuroprotective agents, for example, in the treatment and/or prevention of neuro-degenerative disorders arising as consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntingdon's chorea, Alzheimer's disease, amyotrophic lateral sclerosis, Parkinson's disease, olivo-pontocerebellar atrophy, anoxia such as from drowning, spinal cord and head injury, and poisoning by neurotoxins, including environmental neurotoxins.

The compounds of this invention may be useful to prevent and/or treat inflammatory or auto-immune disorders such as psoriasis, dermatitis, asthma and others.

The dosage administered to a patient will normally be determined by the prescribing physician and will generally vary according to the age, weight and response of the individual patient, as well as the severity of the patient's symptoms. However, in most instances, an effective therapeutic daily dosage will be in the range of from about 0.05 mg/kg to about 50 mg/kg of body weight and, preferably, of from 0.5 mg/kg to about 20 mg/kg of body weight administered in single or divided doses. In some cases, however, it may be necessary to use dosages outside these limits.

In the treatment of irritable bowel syndrome, for instance, 0.1 to 10 mg/kg of a CCK antagonist might be administered orally (p.o.), divided into two doses per day (b.i.d.). In treating delayed gastric emptying, the dosage range would probably be the same, although the drug might be administered either intravenously (i.v.) or orally, with the i.v. dose probably tending to be slightly lower due to a better availability. Acute pancreitis might be treated preferentially in an i.v. form, whereas spasm and/or reflex oesophageal, chronic pancreitis, post-vagotomy diarrhoea, anorexia or pain associated with biliary dyskinesia might indicate a p.o. form of administration.

In the effective treatment of panic syndrome, panic disorder, anxiety disorder and the like, preferably about 0.05 mg/kg to about 1.0 mg/kg of CCK antagonist may be administered orally (p.o.), in single or divided doses per day (b.i.d.). Other routes of administration are also suitable.

For directly introducing analgesia, anaesthesia or loss of pain sensation, the effective dosage range is preferably from about 100 ng/kg to about 1 mg/kg by intraperitoneal administration. Oral administration is an alternative route, as well as others.

While it is possible for an active ingredient to be administered alone as the raw chemical, it is preferable to present it as a pharmaceutical formulation. The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulation and not deleterious to the recipient thereof.

Conveniently, unit doses of a formulation contain between 0.1 mg and 1 g of the active ingredient. Preferably, the formulation is suitable for administration from one to six, such as two to four, times per day. For topical administration, the active ingredient preferably comprises from 1% to 2% by weight of the formulation but the active ingredient may comprise as much as 10% w/w. Formulations suitable for nasal or buccal administration, such as the self-propelling powder-dispensing formulations described hereinafter, may comprise 0.1 to 20% w/w, for example about 2% w/w of active ingredient.

The formulations include those in a form suitable for oral, ophthalmic, rectal, parenteral (including subcutaneous, vaginal, intraperitoneal, intramuscular and intravenous), intra-articular, topical, nasal or buccal administration.

Formulations of the present invention suitable for oral administration may be in the form of discrete units such as capsules, cachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be in the form of a bolus, electuary or paste. For such formulations, a range of dilutions of the active ingredient in the vehicle is suitable, such as from 1% to 99%, preferably 5% to 50% and more preferably 10% to 25% dilution. Depending upon the level of dilution, the formulation will be either a liquid at room temperature (in the region of about 20° C.) or a low-melting solid.

Formulations for rectal administration may be in the form of a suppository incorporating the active ingredient and a carrier such as cocoa butter, or in the form of an enema.

Formulations suitable for parenteral administration comprise a solution, suspension or emulsion, as described above, conveniently a sterile aqueous preparation of the active ingredient that is preferably isotonic with the blood of the recipient.

Formulations suitable for intra-articular administration may be in the form of a sterile aqueous preparation of the active ingredient, which may be in a microcrystalline form, for example, in the form of an aqueous microcrystalline suspension or as a micellar dispersion or suspension. Liposomal formulations or biodegradable polymer systems may also be used to present the active ingredient particularly for both intra-articular and ophthalmic administration.

Formulations suitable for topical administration include liquid or semi-liquid preparations such as liniments, lotions or applications; oil-in-water or water-in-oil emulsions such as creams, ointments or pastes; or solutions or suspensions such as drops. For example, for ophthalmic administration, the active ingredient may be presented in the form of aqueous eye drops, as for example, a 0.1-1.0% solution.

Drops according to the present invention may comprise sterile aqueous or oily solutions. Preservatives, bactericidal and fungicidal agents suitable for inclusion in the drops are phenylmercuric salts (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the eye. An eye lotion may comprise a sterile aqueous solution optionally containing a bactericide or preservative prepared by methods similar to those for the preparation of drops. Lotions or liniments for application to the skin may also include an agent to hasten drying and to cool the skin, such as an alcohol, or a softener or moisturiser such as glycerol or an oil such as castor oil or arachis oil.

Creams, ointments or pastes according to the present invention are semi-solid formulations of the active ingredient in a base for external application. The base may comprise one or more of a hard, soft or liquid paraffin, glycerol, beeswax, a metallic soap; a mucilage; an oil such as a vegetable oil, eg almond, corn, arachis, castor or olive oil; wool fat or its derivatives; or a fatty acid ester of a fatty acid together with an alcohol such as propylene glycol or macrogols. The formulation may also comprise a suitable surface-active agent, such as an anionic, cationic or non-ionic surfactant such as a glycol or polyoxyethylene derivatives thereof. Suspending agents such as natural gums may be incorporated, optionally with other inorganic materials, such as silicaceous silicas, and other ingredients such as lanolin.

Formulations suitable for administration to the nose or buccal cavity include those suitable for inhalation or insufflation, and include powder, self-propelling and spray formulations such as aerosols and atomisers. The formulations, when dispersed, preferably have a particle size in the range of 10 to 200 g.

Such formulations may be in the form of a finely comminuted powder for pulmonary administration from a powder inhalation device or self-propelling powder-dispensing formulations, where the active ingredient, as a finely comminuted powder, may comprise up to 99.9% w/w of the formulation.

Self-propelling powder-dispensing formulations preferably comprise dispersed particles of solid active ingredient, and a liquid propellant having a boiling point of below 18° C. at atmospheric pressure. Generally, the propellant constitutes 50 to 99.9% w/w of the formulation whilst the active ingredient constitutes 0.1 to 20% w/w. for example, about 2% w/w, of the formulation.

The pharmaceutically acceptable carrier in such self-propelling formulations may include other constituents in addition to the propellant, in particular a surfactant or a solid diluent or both. Surfactants are desirable since they prevent agglomeration of the particles of active ingredient and maintain the active ingredient in suspension. Especially valuable are liquid non-ionic surfactants and solid anionic surfactants or mixtures thereof. Suitable liquid non-ionic surfactants are those having a hydrophile-lipophile balance (HLB, see Journal of the Society of Cosmetic Chemists Vol. 1 pp. 311-326 (1949)) of below 10, in particular esters and partial esters of fatty acids with aliphatic polyhydric alcohols. The liquid non-ionic surfactant may constitute from 0.01 up to 20% w/w of the formulation, though preferably it constitutes below 1% w/w of the formulation. Suitable solid anionic surfactants include alkali metal, ammonium and amine salts of dialkyl sulphosuccinate and alkyl benzene sulphonic acid. The solid anionic surfactants may constitute from 0.01 up to 20% w/w of the formulation, though preferably below 1% w/w of the composition. Solid diluents may be advantageously incorporated in such self-propelling formulations where the density of the active ingredient differs substantially from the density of the propellant; also, they help to maintain the active ingredient in suspension. The solid diluent is in the form of a fine powder, preferably having a particle size of the same order as that of the particles of the active ingredient. Suitable solid diluents include sodium chloride, sodium sulphate and sugars.

Formulations of the present invention may also be in the form of a self-propelling formulation wherein the active ingredient is present in solution. Such self-propelling formulations may comprise the active ingredient, propellant and co-solvent, and advantageously an antioxidant stabiliser. Suitable co-solvents are lower alkyl alcohols and mixtures thereof. The co-solvent may constitute 5 to 40% w/w of the formulation, though preferably less than 20% w/w of the formulation. Antioxidant stabilisers may be incorporated in such solution-formulations to inhibit deterioration of the active ingredient and are conveniently alkali metal ascorbates or bisulphites. They are preferably present in an amount of up to 0.25% w/w of the formulation.

Formulations of the present invention may also be in the form of an aqueous or dilute alcoholic solution, optionally a sterile solution, of the active ingredient for use in a nebuliser or atomiser, wherein an accelerated air stream is used to produce a fine mist consisting of small droplets of the solution. Such formulations usually contain a flavouring agent such as saccharin sodium and a volatile oil. A buffering agent such as sodium metabisulphite and a surface-active agent may also be included in such a formulation which should also contain a preservative such as methylhydroxybenzoate.

Other formulations suitable for nasal administration include a powder, having a particle size of 20 to 500 microns, which is administered in the manner in which snuff is taken, ie by rapid inhalation through the nasal passage from a container of the powder held close up to the nose.

In addition to the aforementioned ingredients, the formulations of this invention may include one or more additional ingredients such as diluents, buffers, flavouring agents, binders, surface active agents, thickeners, lubricants, preservatives eg methylhydroxybenzoate (including anti-oxidants), emulsifying agents and the like. A particularly preferred carrier or diluent for use in the formulations of this invention is a lower alkyl ester of a $C_{18}$ to $C_{24}$ mono-unsaturated fatty acid, such as oleic acid, for example ethyl oleate. Other suitable carriers or diluents include capric or caprylic esters or triglycerides, or mixtures thereof, such as those caprylic/capric triglycerides sold under the trade name Miglyol, eg Miglyol 810.

Because these compounds antagonise the function of CCK in animals, they may also be used as feed additives to increase the food intake of animals, such as in a daily dosage of from about 0.05 to 50 mg/kg of body weight.

The invention will now be further described by way of example only.

The compounds of formula (I) can be prepared by reaction of appropriately-substituted furan-2(5H)-ones with the corresponding amine, as illustrated in scheme 1 below.

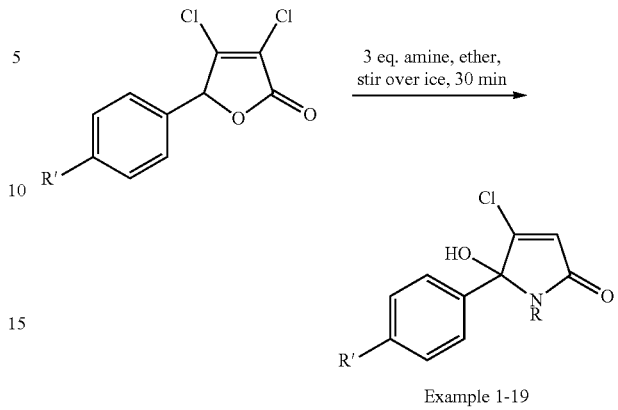

Example 1-19

$R' = H, Cl$

Examples of pyrolones 1-19 are prepared from Examples 1 and 2 and the experimental details are included in the selected examples.

A chloro substituent in the p-position enhanced the CCK binding affinity. The substituent R enabled binding affinity of the molecules and allowed to control CCK A CCK B selectivity.

Starting material are the commercially available mucochloric acid, mucobromic acid and furfural. Furfural can be converted into 5-hydroxy-4-chloro-2(5H)-furanone according to published methods.

The first step is the preparation of building blocks.

Intensive investigations were performed on the chemistry of mucochloric acid, from 1880 to 1905 by Hill and Simonis, but was not again studied further until the 1950's by Mowry [Mowry, D. T., (1950), J. Am. Chem. Soc. 2535-3537 and Mowry, D. T., (1953), J. Am. Chem. Soc. 1909-1910]. Mowry stated that mucochloric acid is thought to be in the half aldehyde state of dichloromaleic acid and is thought to exist in the open and closed ring forms (Scheme 2)

Preparation of
3,4-dichloro-5-phenylfuran-2(5H)-one

The Friedel crafts reaction conditions was utilised to prepare 3,4-dichloro-5-phenylfuran-2(5H)-one according to the published method by Semonsky et al. [Semonsky, M.; Rockova, E.; Cerny, A.; Kakac, B. and Macek, K. (1961), Collec. Czech. Chem. Commun. 27, 1939-1954.]. Mucochloric acid was dissolved in benzene, which acts a both solvent and reagent, with aluminium chloride. The mixture was allowed to stir at RT for 3 days, under inert conditions. After work up a brown oil was recrystallised from ethanol to give white crystals, 54% yield. Analysis of the product was initially achieved by APCI+ mass-spectrometry, where the MS+H was just detectable and subsequently confirmed by both $^1$H and $^{13}$C NMR spectroscopy.

Chlorinated 2(5H)-furanones were prepared accordingly.

General Synthesis Methods

The majority of chemicals used were obtained from the laboratory and chemical stores. The remainder were ordered from Aldrich Catalogue Handbook of Fine Chemicals and Lancaster 1999/2000/2001.

Mass spectrometric analyses were obtained by Atmospheric Pressure Chemical Ionisation (APCI), negative or positive mode, using a Hewlett-Packard 5989b quadrupole instrument. This was connected to an electrospray 59987A unit with automatic injection (Hewlett-Packard 1100 series autosampler). Samples were dissolved in HPLC grade methanol, toluene or acetonitrile.

Both Proton and Carbon NMR spectra were obtained on a Brucker AC 250 instrument, operating at 250 MHz, calibrated with the solvent reference peak or TMS.

IR spectra were plotted from KBr discs on a Mattson 300 FTIR Spectrophotometer. Melting points were recorded from a Stuart Scientific Melting Point (SMP1) and are uncorrected.

Analytical Thin Layer Chromatography was obtained using aluminium sheets, silica gel$_{60}$ F254 and visualized using ultraviolet light.

Preparative chromatography was performed on 250 μm, 20×20 cm silica gel TLC plates from Aldrich.

Small scale solution syntheses were carried out on a carousel reaction station (RR 98030), comprising a 12-place carousel reaction station and reflux head, and 12× flexible tubing from Radleys, on a RCT basic hotplate from IKA Labortechnik with IKATRON ETS D3 temperature controller or using heating blocks (TECHNE Dri-block DB-3A).

Preparation of 4-Chloro-5-hydroxy-5-aryl-1,5-dihydro-pyrrol-2-ones

The compounds were prepared according to scheme 1 and a general method towards the synthesis of the target molecules is outlined below.

General Method:

The relevant amine (3 times excess) was added to a solution of building block (0.7 mol) in ether (10 ml) and it was stirred on ice for 30 minutes. It was allowing to warm up to RT over the time. The resultant mixture was poured into 5 ml water and separated by a separating funnel. The mixture was washed with water three times. The organic layer was dried over magnesium sulphate and the solvent was removed under vacuum. All compounds gave an oily solid which were passed through a column (80% ether, 20% petrol ether). The resulting fractions were dried from excess solvent under vacuum to yield crystals.

Active Molecules

EXAMPLE 1

4-Chloro-1-cyclopropyl-5-hydroxy-5-phenyl-1,5-dihydro-pyrrol-2-one

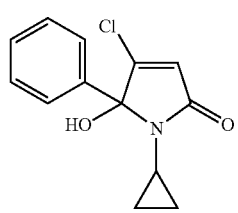 [SMILES: O=C1C=C(Cl)C(O)(c2ccccc2)N1C1CC1]

Yield=83%
Melting Point: 177-179° C.
$R_f$ (80% ether/20% petrol ether)=0.24
Molecular Weight: 249.7
Molecular Formula: $C_{13}H_{12}ClNO_2$
MS (APCI(+)): 193/195 (M+1), 250/252 (M+) m/z
$^1$H NMR (CDCl$_3$) 250 MHz: δ=7.31-7.49 (ArH, 5H), 6.09 (s, CH), 3.41-3.50 (C—OH), 2.08-2.21 (m, N—CH), 0.95-1.04 & 0.38-0.69 (m, CH$_2$, 4H) p.p.m.
$^{13}$C NMR (CDCl$_3$) 250 MHz: δ=167.4 (C=O), 154.8 (C—Cl), 135.2 (ArC), 129.2 (2×ArC), 128.8 (2×ArC), 126.1 (ArC), 122.2 (CH—CCl), 93.5 (C—OH), 22.6 (N—CH), 3.8, 5.1 (CH$_2$, 2C) p.p.m.
IR (KBr-disc) υ max: 3416, 3260, 3105, 3011, 2363, 2338, 1671, 1602, 1490, 1450, 1409, 1369, 1256, 1144, 1032, 939, 833, 752, 702 cm$^{-1}$.

EXAMPLE 2

4-Chloro-1-(3,4-dimethyl-phenyl)-5-hydroxy-5-phenyl-1,5-dihydro-pyrrol-2-one

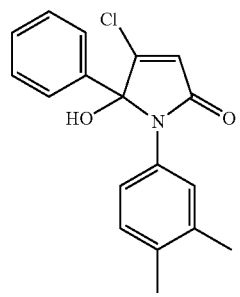 [SMILES: Cc1ccc(N2C(=O)C=C(Cl)C2(O)c2ccccc2)cc1C]

Yield=49%
M.P: 168-171° C.
$R_f$ (80% ether/20% petrol ether)=0.19
Molecular Weight: 313.8
Molecular Formula: $C_{18}H_{16}ClNO_2$
MS (APCI(+)): 193/195 (M+1), 314/316 (M+) m/z
$^1$H NMR (CDCl$_3$) 250 MHz: δ=7.41-7.52 (m, Ar—H, 2H), 7.30-7.38 (m, Ar—H, 3H), 7.18 (s, Ar—H, 1H), 6.92-7.01 (m, Ar—H, 2H), 6.38 (s, CH—O), 3.68-3.73 (bs, C—OH), 2.13-2.27 (m, CH$_3$, 6H) p.p.m.
$^{13}$C NMR (CDCl$_3$) 250 MHz: δ=168.9 (C=O), 159.7 (C—Cl), 136.9 (ArC), 135.1 (ArC), 132.4 (ArC), 129.9 (ArC), 129.0 (2×ArC), 126.9 (ArC), 126.1 (2×ArC), 123.0 (ArC) 122.2 (CH—CCl), 93.5 (C—OH), 19.9 (Ar—CH$_3$), 19.3 (Ar—CH$_3$) p.p.m.
IR (KBr-disc) υ max: 3517, 3357, 3114, 2840, 2674, 2361, 2342, 1678, 1607, 1464, 1412, 1361, 1208, 1138, 1071, 988, 755, 700 cm$^{-1}$.

EXAMPLE 3

4-Chloro-5-hydroxy-1-isopropyl-5-phenyl-1,5-dihydro-pyrrol-2-one

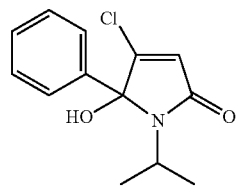 [SMILES: CC(C)N1C(=O)C=C(Cl)C1(O)c1ccccc1]

Yield=79%
Melting Point: 163-165° C.
$R_f$ (80% ether/20% petrol ether)=0.26
Molecular Weight: 251.7
Molecular Formula: $C_{13}H_{14}ClNO_2$
MS (APCI(+)): 193/195 (M+1), 252/254 (M+) m/z
$^1$H NMR (CDCl$_3$) 250 MHz: δ=7.40-7.51 (m, ArH, 5H), 6.14 (s, CH), 3.71-3.79 (bs, OH), 3.42-3.59 (m, N—CH, J=7.5 Hz), 1.33-1.48 & 1.21-1.28 (d, CH$_3$, 6H) p.p.m.
$^{13}$C NMR (CDCl$_3$) 250 MHz: δ=167.5, 155.0, 135.0, (ArC), 129.1 (2×ArC), 128.5 (2×ArC), 126.4 (ArC), 122.4 (CH—CCl), 93.4 (C—OH), 45.6 (N—CH), 21.1, 20.0 (CH$_3$, 2×C) p.p.m.
IR (KBr-disc) υ max: 3227, 2990, 2940, 2365, 2350, 1956, 1693, 1615, 1456, 1428, 1247, 1131, 1072, 1009, 934, 847, 747, 697 cm$^{-1}$.

EXAMPLE 4

4-Chloro-5-hydroxy-1-methyl-5-phenyl-1,5-dihydro-pyrrol-2-one

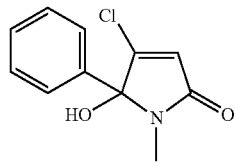

Yield=75%
Melting Point: 146-148° C.
$R_f$ (80% ether/20% petrol ether)=0.26
Molecular Weight: 223.7
Molecular Formula: $C_{11}H_{10}ClNO_2$
MS (APCI(+)): 193/195 (M+1), 224/226 (M+) m/z
$^1$H NMR (DMSO-d$_6$)) 250 MHz: δ=7.29-7.48 (m, ArH, 5H), 6.49 (s, CH), 2.08 (s, CH$_3$) p.p.m.
$^{13}$C NMR (CDCl$_3$) 250 MHz: δ=168.1 (C=O), 156.4 (C—Cl), 134.1 (ArC), 129.4 (2×ArC), 128.9 (2×ArC), 126.2 (ArC), 121.3 (CH—Cl), 92.6 (C—OH), 24.5 (CH$_3$) p.p.m.
IR (KBr-disc) υ max: 3224, 3110, 2952, 2820, 2617, 2375, 2339, 1975, 1697, 1605, 1453, 1438, 1258, 1207, 1065, 992, 856, 764, 704 cm$^{-1}$.

EXAMPLE 5

4-Chloro-5-hydroxy-1-phenethyl-5-phenyl-1,5-dihydro-pyrrol-2-one

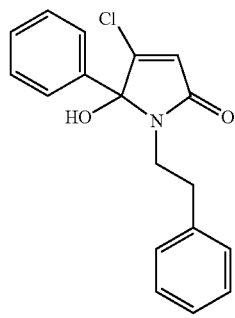 [SMILES: O=C1C=C(Cl)C(O)(c2ccccc2)N1CCc1ccccc1]

Yield=49%
Melting Point: 155-158° C.
$R_f$ (80% ether/20% petrol ether)=0.21
Molecular Weight: 313.8
Molecular Formula: $C_{18}H_{16}ClNO_2$
MS (APCI(+)): 193/195 (M+1), 314/316 (M+) m/z
$^1$H NMR (CDCl$_3$) 250 MHz: δ=7.09-7.53 (m, ArH, 10H), 6.20 (s, CH), 3.64-3.79 (m, N—CH$_2$, 1H), 2.88-3.29 (m, overlapping OH & Ar—CH$_2$, 3H), 2.60-2.75 (m, N—CH$_2$, 1H) p.p.m.
$^{13}$C NMR (CDCl$_3$) 250 MHz: δ=168.0 (C=O), 155.7 (C—Cl), 139.0 (ArC), 134.6 (ArC), 129.4 (2×ArC), 128.85 (2×ArC), 128.84 (2×ArC), 128.6 126.6 (2×ArC), 126.2 (2×ArC), 121.8 (CH—CCl), 92.7 (C—OH), 41.9 (N—CH$_2$), 34.6 (Ar—CH$_2$) p.p.m.
IR (KBr-disc) υ max: 3433, 3246, 2929, 2366, 2334, 1681, 1658, 1607, 1455, 1406, 1251, 1151, 1128, 1066, 931, 753, 699 cm$^{-1}$.

EXAMPLE 6

4-Chloro-1-hexyl-5-hydroxy-5-phenyl-1,5-dihydro-pyrrol-2-one

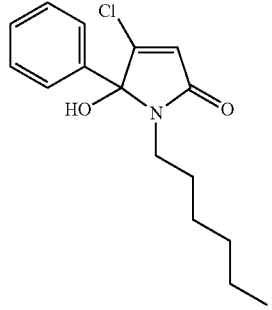 [SMILES: CCCCCCN1C(=O)C=C(Cl)C1(O)c1ccccc1]

Yield=51%
Melting Point: 173-175° C.
$R_f$ (80% ether/20% petrol ether)=0.28
Molecular Weight: 293.8
Molecular Formula: $C_{16}H_{20}ClNO_2$
MS (APCI(+)): 193/195 (M+1), 294/296 (M+) m/z $^1$H NMR (CDCl$_3$) 250 MHz: δ=7.40-7.52 (m, ArH, 5H), 6.15 (s, CH), 4.76-4.82 (bs, OH), 3.28-3.49 (m, CH$_2$, 1H), 2.91-3.08 (m, CH$_2$, 1H), 1.09-1.59 (m, CH$_2$, overlapping, 8H), 0.78-0.92 (t, CH$_3$, J=7.1 Hz) p.p.m.
$^{13}$C NMR (CDCl$_3$) 250 MHz: δ=168.0 (C=O), 155.6 (C—Cl), 134.9 (ArC), 129.2 (2×ArC), 128.7 (2×ArC), 126.2 (ArC), 121.8 (CH—Cl), 93.0 (C—OH), 40.2, 31.3, 28.7, 26.8, 22.5 (CH$_2$, 5×C), 14.0 (CH$_3$) p.p.m.

IR (KBr-disc) υ max: 3245, 2930, 2865, 1689, 1658, 1494, 1453, 1412, 1365, 1321, 1150, 1069, 927, 753, 696 cm$^{-1}$.

EXAMPLE 7

4-Chloro-1-cyclopentyl-5-hydroxy-5-phenyl-1,5-dihydro-pyrrol-2-one

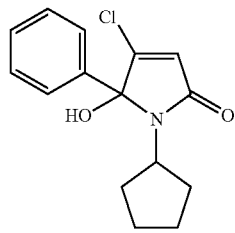 [SMILES: O=C1C=C(Cl)C(O)(c2ccccc2)N1C1CCCC1]

Yield=81%
Melting Point: 180-182° C.
$R_f$ (80% ether/20% petrol ether)=0.26
Molecular Weight: 277.8
Molecular Formula: $C_{15}H_{16}ClNO_2$
MS (APCI(+)): 193/195 (M+1), 278/280 (M+) m/z
$^1$H NMR (CDCl$_3$) 250 MHz: δ=7.39-7.61 (m, ArH, 5H), 6.08 (s, CH), 4.77-4.92 (bs, OH), 3.49-3.68 (m, N—CH, J=8.9 Hz), 1.98-2.17 (m, CH$_2$), 1.71-1.96 (m, CH$_2$, 4H), 1.36-1.55 (m, CH$_2$, 4H) p.p.m.
$^{13}$C NMR (CDCl$_3$) 250 MHz: δ=167.2 (C=O), 155.0 (C—Cl), 135.2 (ArC), 129.1 (2×ArC), 128.6 (2×ArC), 126.5 (ArC), 122.2 (CH—CCl), 93.3 (C—OH), 54.3 (N—CH), 30.0 (CH$_2$), 28.8 (CH$_2$), 24.5, 24.4 (CH$_2$, 2×C) p.p.m.
IR (KBr-disc) υ max: 3220, 2961, 2877, 2373, 2341, 1684, 1613, 1448, 1426, 1248, 1199, 1141, 1070, 934, 850, 750, 701 cm$^{-1}$.

EXAMPLE 8

4-Chloro-5-hydroxy-1-isobutyl-5-phenyl-1,5-dihydro-pyrrol-2-one

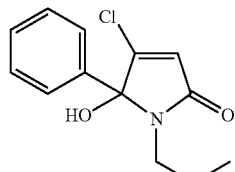

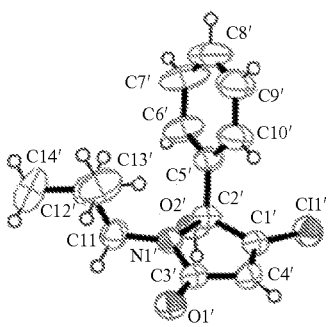

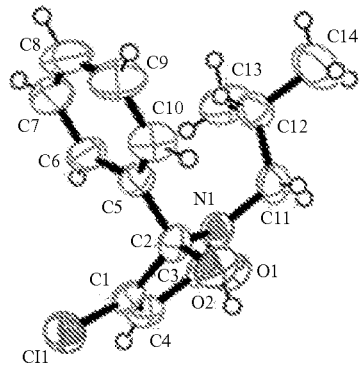

Yield=85%
Melting Point: 167-169° C.
$R_f$ (80% ether/20% petrol ether)=0.27
Molecular Weight: 264.7
Molecular Formula: $C_{14}H_{16}ClNO_2$
MS (APCI(+)): 193/195 (M+1), 266/268 (M+) m/z
$^1$H NMR (CDCl$_3$) 250 MHz: δ=7.38-7.51 (m, ArH, 5H), 6.24 (s, CH), 4.79-4.98 (bs, OH), 3.23-3.32 & 2.18-2.29 (dd, CH$_2$, J=8.1 Hz, 2H), 1.71-1.90 (m, CH—CH$_2$, J=7.4) Hz), 0.76-0.96 (m, CH$_3$, 6H) p.p.m.
$^{13}$C NMR (CDCl$_3$) 250 MHz: δ=168.5 (C=O), 155.7 (CH—CCl), 137.1 (ArC), 129.2, 128.7, 126.2 (5×ArC), 121.7 (CH—CCl), 93.1 (C—OH), 47.6 (CH$_2$), 27.5 (CH—CH$_2$), 20.4 (CH$_3$, 2×C) p.p.m.
IR (KBr-disc) υ max: 3237, 3114, 2965, 2926, 2881, 2374, 2343, 1675, 1614, 1460, 1416, 1299, 1251, 1202, 1150, 1072, 1027, 878, 758, 696 cm$^{-1}$.

Crystal Data—(See section 4.2.2. for structure, sample recrystallised from methanol):

| | |
|---|---|
| $C_{28}H_{32}Cl_2N_2O_4$ | V = 1371.5(5) Å$^3$ |
| $M_r$ = 531.46 | Z = 2 |
| T = 293(2)K | $D_x$ = 1.287 Mg/m$^{-3}$ |
| Tabular | $D_m$ not measured |
| 0.20 × 0.15 × 0.10 mm | R [F$^2$ > 2σ(F$^2$)] = 0.0541 |
| Colourless | wR(F$^2$) = 0.1165 |
| Mo Kα radiation: λ = 0.71073 Å | 5136 reflections |
| Triclinic | 331 parameters |
| P-1 | |
| a = 8.3190(13) Å | |
| b = 12.614(4) Å | |
| c = 13.8106(18) Å | |
| α = 93.049(17) ° | |
| β = 94.791(12) ° | |
| γ = 107.651(19) ° | |

Selected geometric parameters (Å, °)

| Cl(1)-C(1) | 1.696(4) | Cl(1')-C(1') | 1.695(4) |
|---|---|---|---|
| C(1)-C(4) | 1.310(5) | C(1')-C(4') | 1.322(5) |
| C(2)-C(5) | 1.511(5) | C(2')-C(5') | 1.524(5) |
| C(2)-O(2) | 1.410(4) | C(2')-O(2') | 1.400(4) |
| C(3)-O(1) | 1.224(5) | C(3')-O(1') | 1.237(4) |
| N(1)-C(11) | 1.448(5) | N(1')-C(11') | 1.448(5) |

EXAMPLE 9

1-Benzyl-4-chloro-5-hydroxy-5-phenyl-1,5-dihydro-pyrrol-2-one

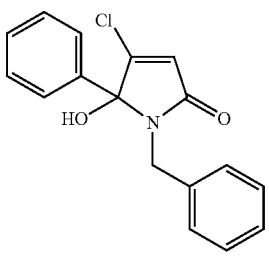 [SMILES: O=C1C=C(Cl)C(O)(c2ccccc2)N1Cc1ccccc1]

Yield=71%
Melting Point: 165-167° C.
$R_f$(80% ether/20% petrol ether)=0.21
Molecular Weight: 299.8
Molecular Formula: $C_{17}H_{14}ClNO_2$
MS (APCI(+)): 193/195 (M+1), 300/302 (M+) m/z
$^1$H NMR (CDCl$_3$) 250 MHz: δ=7.31-7.42 (m, ArH, 5H), 7.14-7.27 (m, ArH, 5H), 6.08 (s, CH), 4.59-4.70 (d, CH$_2$, 1H), 3.93-4.09 (d, CH$_2$, 1H), 3.52-3.79 (bs, OH) p.p.m.
$^{13}$C NMR (CDCl$_3$) 250 MHz: δ=167.9 (C=O), 155.9 (C—Cl), 137.6 (ArC), 134.4 (ArC), 129.3 (ArC), 128.7 (4×ArC), 128.4 (2×ArC), 128.4 (ArC), 127.3 (ArC), 126.4 (ArC), 93.2 (C—OH), 43.4 (CH$_2$) p.p.m.
IR (KBr-disc) υ max: 3446, 3279, 3098, 2931, 2850, 2374, 2334, 1684, 1611, 1456, 1413, 1349, 1276, 1205, 1128, 1051, 696 cm$^{-1}$.

EXAMPLE 10a (major): 4-Chloro-5-hydroxy-5-phenyl-1-((S)-(−)-1-phenyl-ethyl)-1,5-dihydro-pyrrol-2-one

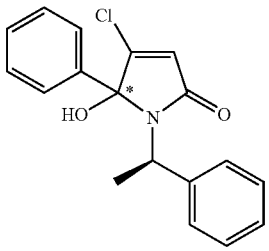 [SMILES: C[C@H](c1ccccc1)N1C(=O)C=C(Cl)C1(O)c1ccccc1]

Yield=66%
Melting Point: 162-164° C.
$R_f$(80% ether/20% petrol ether)=0.23
Molecular Weight: 313.8
Molecular Formula: $C_{18}H_{16}ClNO_2$
MS (APCI(+)): 193/195 (M+1), 314/316 (M+) m/z
$^1$H NMR (CDCl$_3$) 250 MHz: δ=7.34-7.53 (ArH, 7H), 7.08-7.25 (ArH, 3H), 5.96 (s, CH), 4.16-4.28 (q, N—CH, J=7.9 Hz), 2.91-3.37 (bs, OH), 1.49-1.58 (d, CH$_3$) p.p.m.
$^{13}$C NMR (CDCl$_3$) 250 MHz: δ=167.3 (C=O), 154.3 (C—Cl), 142.5 (ArC), 134.7 (ArC), 129.4 (ArC), 128.7 (2×ArC), 128.4 (2×ArC), 127.7 (2×ArC), 127.3 (2×ArC), 126.4 (ArC), 123.0 (CH—CCl), 93.8 (C—OH), 53.5 (NH—CH), 18.8 (CH$_3$) p.p.m.

IR (KBr-disc) υ max: 3241, 2983, 2932, 2863, 2366, 2347, 1686, 1661, 1614, 1494, 1456, 1425, 1356, 1258, 1202, 1025, 931, 855, 755, 692 cm$^{-1}$.

EXAMPLE 10b (minor): 4-Chloro-5-hydroxy-5-phenyl-1-((S)-(−)-1-phenyl-ethyl)-1,5-dihydro-pyrrol-2-one

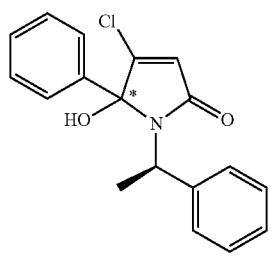 [SMILES: C[C@H](c1ccccc1)N1C(=O)C=C(Cl)C1(O)c1ccccc1]

Yield=8%
$R_f$(80% ether/20% petrol ether)=0.23
Molecular Weight: 313.8
Molecular Formula: $C_{18}H_{16}ClNO_2$
MS (APCI(+)): 193/195 (M+1), 314/316 (M+) m/z
$^1$H NMR (CDCl$_3$) 250 MHz: δ=7.29-7.53 (ArH, 7H), 6.95-7.21 (ArH, 3H), 6.08 (s, CH), 4.59-4.78 (q, N—CH, J=7.9 Hz), 6.62-2.71 (bs, OH), 1.49-1.63 (d, CH$_3$) p.p.m.

EXAMPLE 11

4-Chloro-1-cyclohexyl-5-hydroxy-5-phenyl-1,5-dihydro-pyrrol-2-one

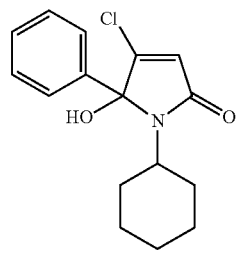 [SMILES: O=C1C=C(Cl)C(O)(c2ccccc2)N1C1CCCCC1]

Yield=57%
Melting Point: 170-172° C.
$R_f$(80% ether/20% petrol ether)=0.27
Molecular Weight: 291.8
Molecular Formula: $C_{16}H_{18}ClNO_2$
MS (APCI(+)): 193/195 (M+1), 292/294 (M+) m/z
$^1$H NMR (CDCl$_3$) 250 MHz: δ=7.26-7.61 (m, ArH, 5H), 6.08 (s, CH), 3.72-3.85 (bs, OH), 2.83-3.19 (m, N—CH), 1.21-2.07 (m, overlapping CH$_2$, 10H) p.p.m.
$^{13}$C NMR (CDCl$_3$) 250 MHz: δ=163.9 (C=O), 153.9 (C—Cl), 135.0 (ArC), 129.25 (2×ArC), 128.9 (2×ArC), 126.4 (ArC), 122.9 (CH—CCl), 96.0 (C—OH), 53.6 (N—CH), 32.8 (CH$_2$), 31.1 (CH$_2$), 29.8 (CH$_2$), 26.2 (2×CH$_2$), 24.2 (CH$_2$) p.p.m.

IR (KBr-disc) υ max: 3440, 2924, 2858, 2355, 2344, 1641, 1449, 1367, 1250, 1138, 1016, 996, 742, 695 cm$^{-1}$.

EXAMPLE 12

4-Chloro-5-(4-chloro-phenyl)-1-cyclopropyl-5-hydroxy-1,5-dihydro-pyrrol-2-one

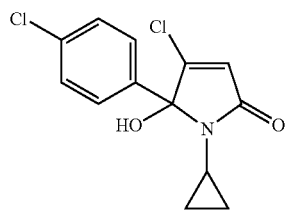 [SMILES: O=C1C=C(Cl)C(O)(c2ccc(Cl)cc2)N1C1CC1]

Yield=72%
Melting Point: 169-171° C.
$R_f$ (80% ether/20% petrol ether)=0.19
Molecular Weight: 284.1
Molecular Formula: $C_{13}H_{11}Cl_2NO_2$
MS (APCI(+)):227/229/231 (M+1), 284/286/288 (M+) m/z
$^1$H NMR (CDCl$_3$) 250 MHz: δ=7.12-7.32 (m, ArH, 4H), 5.97 (s, CH), 3.98-4.16 (bs, OH, 1.67-1.82 (m, N—CH), 0.24-0.99 (m, overlapping CH$_2$, 4H) p.p.m.
$^{13}$C NMR (CDCl$_3$) 250 MHz: δ=165.8 (C=O), 155.4 (C—Cl), 144.2 (ArC), 133.7 (ArC), 129.0 (2×ArC), 127.7 (2×ArC), 122.2 (CH—CCl), 91.7 (C—OH), 22.6 (N—CH), 3.7 & 5.2 (CH$_2$, 2×C) p.p.m.
IR (KBr-disc) υ max: 3433, 3220, 3019, 2935, 2858, 1700, 1675, 1497, 1412, 1251, 1209, 1144, 1089, 1015, 940, 844, 802, 679 cm$^{-1}$.

EXAMPLE 13

4-Chloro-5-(4-chloro-phenyl)-5-hydroxy-1-isopropyl-1,5-dihydro-pyrrol-2-one

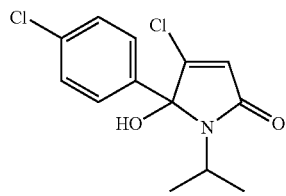 [SMILES: CC(C)N1C(=O)C=C(Cl)C1(O)c1ccc(Cl)cc1]

Yield=69%
Melting Point: 127-130° C.
$R_f$ (80% ether/20% petrol ether)=0.21
Molecular Weight: 286.2
Molecular Formula: $C_{13}H_{13}Cl_2NO_2$
MS (APCI(+)):227/229231 (M+1), 286/288/290 (M+) m/z
$^1$H NMR (CDCl$_3$) 250 MHz: δ=7.31-7.48 (m, ArH, 4H), 6.06 (s, CH), 3.33-3.52 (m, N—CH), 1.25-1.37 & 1.10-1.22 (d, CH$_3$, 6H), (OH not detected) p.p.m.
$^{13}$C NMR (CDCl$_3$) 250 MHz: δ=167.1 (C=O), 154.0 (C—Cl), 136.7 (ArC), 133.4 (ArC), 128.9 (2×ArC), 128.0 (2×ArC), 123.2 (CH—CCl), 92.9 (C—OH), 45.6 (N—CH), 20.1 & 21.3 (CH$_3$, 2×C) p.p.m.

IR (KBr-disc) υ max: 3272, 2978, 2927, 1691, 1614, 1496, 1429, 1384, 1352, 1249, 1096, 1012, 936, 846, 801, 683 cm$^{-1}$.

EXAMPLE 14

4-Chloro-5-(4-chloro-phenyl)-5-hydroxy-1-methyl-1,5-dihydro-pyrrol-2-one

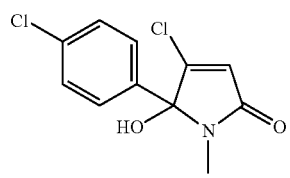 [SMILES: CN1C(=O)C=C(Cl)C1(O)c1ccc(Cl)cc1]

Yield=66%
Melting Point: 179-181° C.
$R_f$ (80% ether/20% petrol ether)=0.24
Molecular Weight: 258.1
Molecular Formula: $C_{11}H_9Cl_2NO_2$
MS (APCI(+)): 227/229/231 (M+1), 258/260/262 (M+) m/z
$^1$H NMR (CDCl$_3$) 250 MHz: δ=7.31-7.42 (ArH, 4H), 6.06 (s, CH), 4.56-4.71 (bs, OH), 2.60 (s, CH$_3$) p.p.m.
$^{13}$C NMR (CDCl$_3$) 250 MHz: δ=167.8 (C=O), 156.0 (C—Cl), 135.5 (ArC), 132.8 (ArC), 129.1 (2×ArC), 127.8 (2×ArC), 121.6 (CH—CCl), 92.2 (C—OH), 24.4 (CH$_3$) p.p.m.
IR (KBr-disc) υ max: 3429, 3102, 2970, 2932, 2857, 1677, 1611, 1494, 1475, 1431, 1202, 1151, 1091, 988, 928, 811, 692 cm$^{-1}$.

EXAMPLE 15

4-Chloro-5-(4-chloro-phenyl)-5-hydroxy-1-phenethyl-1,5-dihydro-pyrrol-2-one

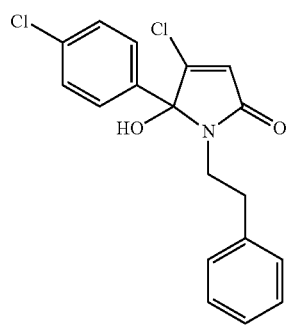 [SMILES: O=C1C=C(Cl)C(O)(c2ccc(Cl)cc2)N1CCc1ccccc1]

Yield=45%
Melting Point: 145-148° C.
$R_f$ (80% ether/20% petrol ether)=0.18
Molecular Weight: 348.2
Molecular Formula: $C_{18}H_{15}Cl_2NO_2$
MS (APCI(+)): 227/229/231 (M+1), 348/350/352 (M+) m/z ¹H NMR (CDCl₃) 250 MHz: δ=7.22-7.49 (m, ArH, 7H), 7.12-7.18 (m, ArH, 2H), 6.13 (s, CH), 3.68-3.79 & 2.64-2.77 (m, N—CH₂), 2.88-3.29 (m, Ar—CH₂), (OH not detected) p.p.m.

¹³C NMR (CDCl₃) 250 MHz: δ=167.7 (C=O), 155.5 (C—Cl), 138.8 (ArC), 135.5 (ArC), 133.3 (ArC), 129.1 (2×ArC), 128.8 (2×ArC), 128.7 (2×ArC), 127.7 (2×ArC), 126.7 (ArC), 121.9 (CH—CCl), 92.3 (C—OH), 42.0 (N—CH₂), 34.5 (Ar—CH₂) p.p.m.

IR (KBr-disc) υ max: 3421, 3228, 2925, 2848, 2370, 2338, 1684, 1658, 1606, 1461, 1406, 1248, 1190, 1097, 935, 806, 697 cm⁻¹.

EXAMPLE 16

4-Chloro-5-(4-chloro-phenyl)-1-hexyl-5-hydroxy-1,5-dihydro-pyrrol-2-one

Yield=49%
Melting Point: 169-172° C.
R$_f$(80% ether/20% petrol ether)=0.25
Molecular Weight: 328.2
Molecular Formula: C₁₆H₁₉Cl₂NO₂
MS (APCI(+)): 227/229/231 (M+1), 328/330/332 (M+) m/z ¹H NMR (CDCl₃) 250 MHz: δ=7.31-7.43 (m, ArH, 4H), 6.15 (s, CH), 3.24-3.44 (m, CH₂, 1H), 2.67-2.91 m, CH₂, 1H), 1.04-1.69 (m, overlapping CH₂, 8H), 0.74-0.89 (t, CH₃, J=6.3 Hz) p.p.m.

¹³C NMR (CDCl₃) 250 MHz: δ=165.8 (C=O), 155.7 (C—Cl), 140.8 (ArC), 136.9 (ArC), 129.1 (2×ArC), 127.8 (2×ArC), 91.6 (C—OH), 40.3 (N—CH₂), 30.8 (N—CH₂—CH₂), 29.1 (N—CH₂—CH₂—CH₂), 26.8 (NH—CH₂—CH₂—CH₂), 22.6 (CH₃—CH₂), 15.2 (CH₃) p.p.m.

IR (KBr-disc) υ max: 3446, 2935, 2863, 1698, 1413, 1252, 1200, 1138, 1092, 1013, 938, 846, 814, 702 cm⁻¹.

EXAMPLE 17

4-Chloro-5-(4-chloro-phenyl)-1-cyclopentyl-5-hydroxy-1,5-dihydro-pyrrol-2-one

Yield=73%
Melting Point: 157-159° C.
R$_f$(80% ether/20% petrol ether)=0.23
Molecular Weight: 312.2
Molecular Formula: C₁₅H₁₅Cl₂NO₂
MS (APCI(+)): 227/229/231 (M+1), 312/314/316 (M+) m/z ¹H NMR (CDCl₃) 250 MHz: δ=7.32-7.51 (ArH, 4H), 6.03 (s, CH), 4.95-5.03 (bs, OH), 3.41-3.62 (m, N—CH, J=9.26 Hz), 1.97-2.19 (m, CH₂), 1.68-1.93 (m, overlapping CH₂, 8H) p.p.m.

¹³C NMR (CDCl₃) 250 MHz: δ=167.1 (C=O), 154.8 (CH—CCl), 135.2 (ArC), 133.9 (ArC), 128.9 (2×ArC), 128.0 (2×ArC), 122.3 (CH—CO), 93.0 (C—OH), 54.3 (N—CH), 30.0 & 28.9 (N—CH—CH₂, 4×C), 24.5 (N—CH—CH₂—CH₂, 2×C) p.p.m.

IR (KBr-disc) υ max: 3407, 3276, 2968, 2922, 2883, 2379, 2339, 1691, 1491, 1429, 1367, 1249, 1203, 1092, 1013, 932, 843, 787, 709 cm⁻¹.

EXAMPLE 18

4-Chloro-5-(4-chloro-phenyl)-5-hydroxy-1-isobutyl-1,5-dihydro-pyrrol-2-one

Yield=76%
Melting Point: 155-158° C.
R$_f$(80% ether/20% petrol ether)=0.22
Molecular Weight: 300.2
Molecular Formula: C₁₄H₁₅Cl₂NO₂
MS (APCI(+)): 227/229/231 (M+1), 300/302/304 (M+) m/z ¹H NMR (CDCl₃) 250 MHz: δ=7.30-7.41 (m, ArH, 4H), 6.19 (s, CH), 3.13-3.31 (dd, CH₂, J=8.0 Hz, 1H), 2.49-2.62 (dd, CH₂, J=8.0 Hz, 1H), 1.69-1.83 (m, CH, J=5.8 Hz), 0.69-0.80 (t, CH₃, J=4.5 Hz, 6H) p.p.m.

¹³C NMR (CDCl₃) 250 MHz: δ=163.3 (C=O), 156.3 (CH—CCl), 139.4 (ArC), 134.8 (ArC), 129.1 (2×ArC), 127.7 (2×ArC), 122.3 (CH—CCl), 95.0 (C—OH), 47.6 (CH₂), 27.6 (CH—CH₂), 20.4 (CH₃, 2×C) p.p.m

IR (KBr-disc) υ max: 3426, 3252, 2964, 2924, 2850, 1684, 1406, 1209, 1095, 817, 743, 703 cm$^{-1}$.

EXAMPLE 19

1-Benzyl-4-chloro-5-(4-chloro-phenyl)-5-hydroxy-1,5-dihydro-pyrrol-2-one

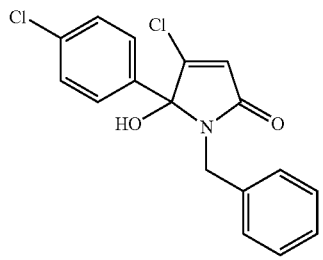 [SMILES: O=C1C=C(Cl)C(O)(c2ccc(Cl)cc2)N1Cc1ccccc1]

Yield=59%
Melting Point: 149-152° C.
$R_f$ (80% ether/20% petrol ether)=0.18
Molecular Weight: 334.2
Molecular Formula: $C_{17}H_{13}Cl_2NO_2$
MS (APCI(+)): 227/229/231 (M+1), 334/336/338 (M+) m/z
$^1$H NMR (CDCl$_3$) 250 MHz: δ=7.29-7.36 (m, ArH, 4H), 7.06-7.25 (m, ArH, 5H), 6.09 (s, CH), 4.52-4.60 (d, CH$_2$, 1H), 3.89-3.98 (d, CH$_2$, 1H) p.p.m.
$^{13}$C NMR (CDCl$_3$) 250 MHz: δ=167.6 (C=O), 155.4 (C—Cl), 137.5 (ArC), 135.3 (ArC), 133.2 (ArC), 129.1 (ArC), 129.0 (ArC), 128.9 (2×ArC), 128.6 (ArC), 128.4 (ArC), 127.9 (2×ArC), 127.4 (ArC), 121.9 (CH), 92.6 (C—OH), 43.2 (CH$_2$) p.p.m.
IR (KBr-disc) υ max: 3442, 2931, 2849, 2365, 2339, 1674, 1616, 1492, 1406, 1349 1272, 1199, 1094, 1018, 817, 699 cm$^{-1}$.

Biological Evaluation—$^{[125]}$I-CCK-8 Receptor Binding Essay

CCK$_A$ and CCK$_B$ receptor binding assays were performed using guinea pig cerebral cortex (CCK$_B$) and rat pancreas (CCK$_A$). Male guinea pig brain tissues were prepared according to the modified method described by Saita et al, [(1994), Eur. J. Pharmacol., 269, 249-254]. Pancreatic membranes were prepared in a similar way described by Charpentier et al, [(1988), Proc Natl Acad Sci USA, 85, 1968-1972]. Briefly, tissues were homogenized in ice cold sucrose (0.32 M, 25 ml) for 15 strokes at 500 rpm and centrifuged at 13000 rpm for 10 mins. The supernatant was re-centrifuged at 13000 rpm for 20 mins. The resulting pellet was re-dispersed to the required volume of buffer at 500 rpm and stored in aliquots at −70° C.

Binding was achieved using a radioligand $^{125}$I-Bolton-Hunter labeled CCK, NEN at 25 pM. The samples were incubated {with membranes (0.1 mg/ml)} in 20 mM Hepes, 1 mM EGTA, 5 mM MgCl$_2$, 150 mm NaCl, 0.25 mg/ml bacitracin at pH 6.5 for 2 hrs at RT and then suspended by centrifugation at 1100 rpm for 5 minutes. The membrane pellets were washed twice with water and the bound radioactivity was measured in a Packard Cobra Auto-gamma counter (B5005). All binding assays were carried out with L-363, 260 as an internal non-specific standard. Controls (no compound) were also added. All samples were made in duplicate and repeated twice. All compounds were initially screened for percentage inhibition at 10 μm. Samples showing an average inhibition of >35% were diluted to 1 μm and re-screened and if active diluted again. This enabled the calculation of IC$_{50}$'s of the series of pyrolones and the examples containing a 5-phenyl group are outlined below.

Active examples

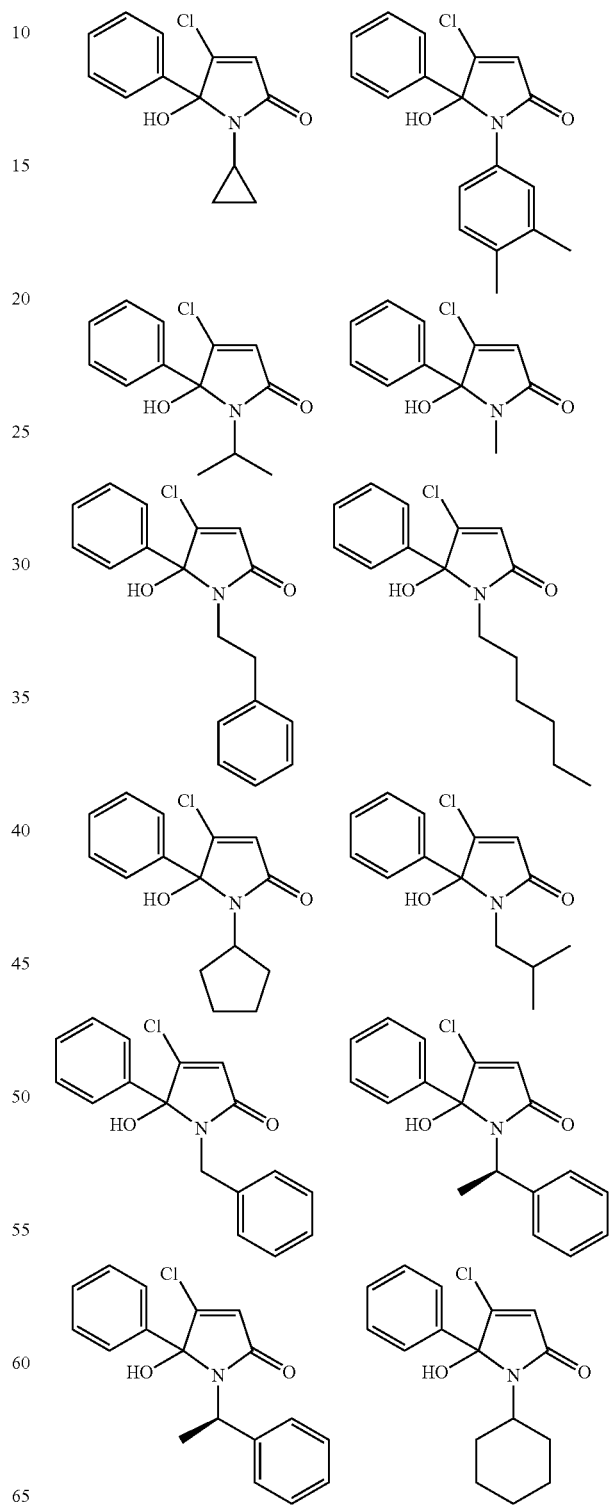

A selection of 11 highly diverse amines were chosen to undergo nucleophilic attack at the carbonyl group of 5-arylated-furan-2-one ring of the furanone building block, leading to ring opening and recyclisation into pyrrol-2-ones. These included aryl amines, one of which has a chiral centre and amines with simple alkyl- and cyclic alkyl side chains. The 5-arylated-5-hydroxy-pyrrol-2-ones being formed here, all contain a chiral centre and therefore will exist as enantiomers. In order to control the stereochemistry a chiral amine, (S)-(–)-phenylethylamine was to be used. Diasteromers were formed, which could be isolated and biologically tested. Isobutylamine and its homologue isopropylamine were also used as the aforementioned amine again has shown good activity in relation to pain, depression and anxiolytic assays.

In summary 3,4-Dichloro-5-phenyl-5H-furan-2-ones were dissolved in ether and cooled on ice. The appropriate amine was added to the cold solution and stirred for 30 minutes, allowing the reaction mixture to slowly warm up to room temperature. After work up, the desired compound was extracted using column chromatography (80% ether, 20% petrol ether) and analysed using NMR, IR and MS.

All outlined compounds are chemically stable, white, crystalline molecules and they are formed in good yields.

The crystalline isopropyl derivative, which contains a chiral centre (5-position), was analysed by X-ray crystallography. X-ray data can be found in the experimental section.

This compound along side the other compounds synthesised here were fully characterised using $^1$H and $^{13}$C NMR, MS and IR spectroscopy.

Pharmacology

Following the synthesis and characterisation of these novel molecules, the evaluation in a receptor binding assay followed and the results are outlined in the table below (Table 2).

TABLE 2

| | Binding affinity | |
|---|---|---|
| Example | Activity CCK-A [µM] | Activity CCK-B [µM] |
| 1 | 2.5 | >10 |
| 2 | 2 | >10 |
| 3 | >10 | >10 |
| 4 | >10 | >10 |
| 5 | 0.020 | 0.020 |
| 6 | >10 | >10 |
| 7 | 0.36 | 0.84 |
| 8 | 4.5 | 0.010 |
| 9 | >10 | >10 |
| 10a | >10 | >10 |
| 10b | >10 | >10 |
| 11 | >10 | >10 |
| 12 | 7.5 | >10 |
| 13 | >10 | >10 |
| 14 | >10 | >10 |
| 15 | 0.002 | 0.0015 |
| 16 | >10 | >10 |
| 17 | 2.5 | >10 |
| 18 | — | — |
| 19 | 2.2 | >10 |

The phenyl-ethyl derivative, example 5, is a potent and mixed CCK antagonist. The binding is enhanced by replacing the phenyl group with p-chlorophenyl and this observation was determined to be a general trend with respect to the analysis of structure-activity-relationships.

Long lipophilic N-substituents resulted in a loss of binding affinity. The Isopropyl derivative 8 showed a good affinity towards the CCK B receptor.

A cycloalkyl substituent on the N showed micromolar affinity, but the affinity was not enhanced further by the introduction of a chlorine atom into the 5 aryl group.

Interestingly, the addition of a methyl group to the benzyl derivative furnished chiral compounds (Example 10a and 10b), which could easily be separated by column chromatography.

The invention claimed is:

1. A compound of formula (I):

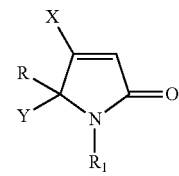

(I)

wherein
X is halogen;
Y is hydroxy group or alkoxy group;
R is phenyl, cyanophenyl, or halogenated phenyl;
$R_1$ is alkyl, branched alkyl, alkenyl, alkynyl, cycloalkyl, alkyloxy, alkylcarbonyl, alkyloxycarbonyl, alkenyl, alkenyloxy, alkenylcarbonyl, phenyl, phenyl alkyl, dialkyl phenyl, benzyl, or benzyl alkyl.

2. The compound as in claim 1, wherein said alkyl-containing moieties are $C_1$-$C_{18}$.

3. The compound as in claim 1, wherein said alkenyl- and said alkynyl-containing moieties are $C_2$-$C_{18}$.

4. The compound as in claim 1, wherein $R_1$ is $C_{1-6}$ alkyl, $C_{1-6}$ alkenyl, $C_{1-6}$ alkynyl, benzyl, cyclohexyl, phenyl, benzyl ($C_{2-4}$)alkyl, or phenyl ($C_{2-4}$) alkyl.

5. "The compounds as in claim 1 wherein X is selected from F, Br, Cl, and I."

6. The compound as in claim 1 having the one of following formula

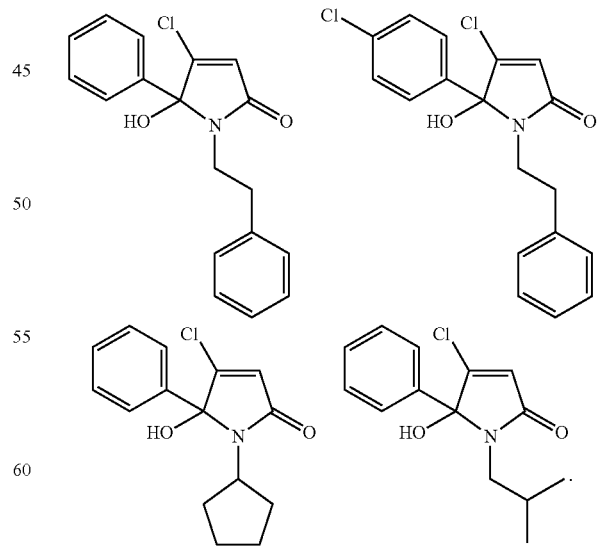

7. The compound of claim 1, wherein X is Cl, F, I, or Br; Y is hydroxyl; R is phenyl, chlorophenyl, bromophenyl, iodophenyl, or cyanophenyl; and $R_1$ is phenyl ethyl.

8. The compound of claim 1, wherein X is Cl, F, I, or Br; Y is hydroxyl; R is phenyl or chlorophenyl; and $R_1$ is cyclopropyl.

9. The compound of claim 1, wherein X is Cl, F, I, or Br; Y is hydroxyl; R is phenyl or chlorophenyl; and $R_1$ is dimethyl phenyl.

10. The compound of claim 1, wherein X is Cl, F, I, or Br; Y is hydroxyl; R is phenyl or chlorophenyl; and $R_1$ is isopropyl.

11. The compound of claim 1, wherein X is Cl, F, I, or Br; Y is hydroxyl; R is phenyl or chlorophenyl; and $R_1$ is methyl.

12. The compound of claim 1, wherein X is Cl, F, I, or Br; Y is hydroxyl; R is phenyl or chlorophenyl; and $R_1$ is hexyl.

13. The compound of claim 1, wherein X is Cl, F, I, or Br; Y is hydroxyl; R is phenyl or chlorophenyl; and $R_1$ is cyclopentyl.

14. The compound of claim 1, wherein X is Cl, F, I, or Br; Y is hydroxyl; R is phenyl, fluorophenyl, iodophenyl, chlorophenyl, or cyanophenyl; and $R_1$ is isobutyl.

15. The compound of claim 1, wherein X is Cl, F, I, or Br; Y is hydroxyl; R is phenyl or chlorophenyl; and $R_1$ is benzyl.

16. The compound of claim 1, wherein X is Cl, F, I, or Br; Y is hydroxyl; R is phenyl or chlorophenyl; and $R_1$ is cyclohexyl.

* * * * *